United States Patent [19]

Sanvordeker et al.

[11] 4,336,243
[45] Jun. 22, 1982

[54] TRANSDERMAL NITROGLYCERIN PAD

[75] Inventors: Dilip R. Sanvordeker, Elk Grove; James G. Cooney, Des Plaines; Ronald C. Wester, Glenview, all of Ill.

[73] Assignee: G. D. Searle & Co., Skokie, Ill.

[21] Appl. No.: 260,517

[22] Filed: May 4, 1981

Related U.S. Application Data

[63] Continuation-in-part of Ser. No. 177,042, Aug. 11, 1980, abandoned.

[51] Int. Cl.³ .................. A61L 15/03; A61F 13/00; A61K 9/70
[52] U.S. Cl. ........................... 424/28; 128/260; 128/268
[58] Field of Search .................. 424/28, 19–22, 424/14, 16; 128/260, 268

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,742,951 | 7/1973 | Zaffaroni | 128/268 |
| 3,972,995 | 8/1976 | Tsuk et al. | 424/28 |
| 3,992,518 | 11/1976 | Chien et al. | 424/22 |
| 4,053,580 | 10/1977 | Chien et al. | 424/22 X |
| 4,291,015 | 9/1981 | Keith et al. | 424/28 |

*Primary Examiner*—Shep K. Rose
*Attorney, Agent, or Firm*—W. Dennis Drehkoff; James G. Passe

[57] ABSTRACT

The present invention provides a trans-dermal delivery pad for nitroglycerin administration, specifically a microsealed, trans-dermal nitroglycerin pad having a backing which is impervious to nitroglycerin absorption and transport and a silicon matrix affixed thereto, said silicone polymer matrix being of cross-linked silicone rubber having from about 10 to 200 micron microsealed compartments being formed by in situ cross-linking of the silicone rubber after it is mixed with a hydrophilic solvent system containing the nitroglycerin and a hydrophobic solvent which enhances nitroglycerin dispersion and transport.

6 Claims, No Drawings

TRANSDERMAL NITROGLYCERIN PAD

This application is a continuation in part of application Ser. No. 177,042 filed Aug. 11, 1980, now abandoned.

BACKGROUND OF THE INVENTION

In recent years, various drug delivery systems have been developed which provide sustained release therapy via a sub-dermal insert. Systems have been disclosed which also provide drug delivery systems suitable for transdermal drug administration.

U.S. Pat. No. 3,964,106, commonly assigned, discloses a microsealed pharmaceutical delivery device suitable for implantation or trans-dermal use, as well as vaginal or intrauterine use.

It has now been found, that in the case of nitroglycerin as the drug to be delivered, drug transport is greatly enhanced and drug delivery increased if triglycerides of saturated coconut oil acids, i.e. miglyol oil 812, and isopropyl palmitate alone, or in combination with mineral oil are added to compliment the hydrophilic solvent system in the polymer matrix.

U.S. Pat. No. 3,996,934 also discloses a medical bandage comprising a backing member and a facing member having at least one reservoir containing systemically active drug either as a distinct layer or as a plurality of microcapsules distributed throughout a silicone polymer matrix. Example one discloses a nitroglycerin pad.

Great Britain Patent Application No. GB 2,021,950 discloses a nitroglycerin bandage containing from 1–10 parts of nitroglycerin per 100 parts of carrier. Mineral oil and lanolin are taught to enhance the transport and absorption of nitroglycerine when the carrier is selected from the group consisting of polyethylene, polypropylene, polybutylene or polymethylbutylene.

Despite the prior art teachings, the only topical form of nitroglycerin commercially available at the present time remains ointments or creams which cause staining and require relatively frequent applications over a much larger surface areas than is required by the nitroglycerin pad of the present invention.

SUMMARY OF THE INVENTION

The present invention provides a transdermal delivery system for the administration of nitroglycerin, and more specifically provides a nitroglycerin pad which is conveniently applied to the skin to provide transdermal nitroglycerin administration over a prolonged period of time.

The pad of the present invention can vary in size depending upon the dosage needs of the individual patient. The preferred size is 2×4 cm. The pad comprises a biologically acceptable silicone polymer matrix having microsealed compartments throughout, the microsealed compartments containing nitroglycerin in a hydrophilic solvent system wherein the ratio of the partition of coefficient of nitroglycerin and the biologically acceptable silicone polymer matrix to the solubility of nitroglycerin in the hydrophilic solvent system is between 1 and $10^{-4}$ ml/mcg. A hydrophobic solvent system is also incorporated to enhance diffusion of the nitroglycerin throughout the matrix. The nitroglycerin is dispersed throughout the matrix, preferably as a nitroglycerin-lactose mixture for ease and safety of handling being diffusable through the biologically acceptable silicon polymer matrix at a therapeutically effective rate when the pad is in contact with the skin. The pad is designed in such a way that the liquid on the surface of the pad acts both as a primary contact between the skin and the pad, as well as a trigger, and promotes diffusion and absorption from the pad and into the skin.

Materials used to form the biologically acceptable polymer container are those capable of forming thin walls or coatings through which pharmaceuticals can pass at a controlled rate. Suitable polymers are biologically and pharmaceutically compatible, non-allergenic and isoluble in and non-irritating to body fluids or tissues with which the device is contacted. The use of soluble polymers is to be avoided since dissolution or erosion of the device would affect the release rate of the pharmaceutical release rate, as well as the capability of the device to remain in place for convenience of removal. Exemplary materials for fabricating the biologically acceptable polymer container include polyethylene, polypropylene, ethylene/propylene copolymers, ethylene/ethylacrylate copolymers, ethylene/vinyl acetate copolymers, silicone rubbers, especially the medical grade polydimethyl siloxanes, neoprene rubber, chlorinated polyethylene, polyvinyl chloride; vinyl chloride copolymers with vinyl acetate, poly methacrylate polymer (hydrogel), vinylidene chloride, ethylene and propylene; polyethylene terephthalate; butyl rubber; epichlorohydrin rubbers; ethylene/vinyl alcohol copolymer; ethylene/vinyloxyethanol copolymer; and the like. For best results, the biologically acceptable polymer container should be selected from polymers of the above classes with glass transition temperatures below room temperature. The polymer may, but need not necessarily, have a degree of crystallinity at room temperature.

The preferred biologically acceptable silicone polymer matrix material is selected from room temperature or elevated temperature cross-linking silicone rubber (polydimethyl siloxane) such as silicone polymers represented by the formula:

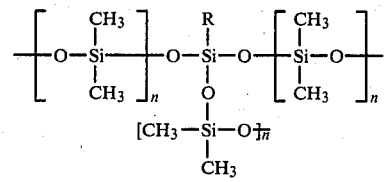

wherein R is $C_1$–$C_7$ alkoxy, vinyl or allyl and wherein n is about 100–5000.

Suitable polymers are capable of forming thin walls or coatings through which nitroglycerin can pass at a controlled rate, are biologically and pharmaceutically compatible, non-allergenic and isoluble in and non-irratating to the skin, and preferably have the following parameters:

| Parameter | Value |
| --- | --- |
| Durometer hardness | 30–100 shore A |
| Tensile Strength | 500–700 psi, Die C |
| Elongation | 100–400%, Die C |
| Tear Strength | 70–100, ppi, Die B |

The hydrophillic solvent system employed in the practice of this invention generally comprises from about 10 to 30 volume percent of polyethylene glycol, preferably polyethylene glycol 400 in distilled water. The hydrophilic solvent system is imbedded with the hydrophobic solvent system within the silicone matrix. The combined solvent systems incorporated within the matrix serve the unique purpose of partitioning and enhancing the diffusion of nitroglycerin throughout the matrix, thereby allowing delivery of nitroglycerin at a controlled rate after the pad has been applied to the skin. Nitroglycerin is then allowed to diffuse through the pad into the skin for absorption to provide the desired pharmacological effect.

The hydrophobic solvent system comprises from about 5 to 15 weight percent of a compound selected from the group consisting of isopropyl palmitate, mineral oil, cholesterol or a triglyceride of a saturated coconut oil acid such as miglyol oil, or a mixture thereof. The incorporation of isopropyl palmitate alone, or in combination with, for example, mineral oil or cholesterol, improves the transport and absorption of nitroglycerin.

It is preferable to admix from about 6 to 22 weight percent of a commercially available 10 percent nitroglycerin-lactose mixture into the hydrophilic solvent system prior to the preparation of the pad of the present invention.

DETAILED DESCRIPTION OF PREFERRED EMBODIMENTS

A preferred embodiment of the present invention is a microsealed, transdermal nitroglycerin pad having a backing which is impervious to nitroglycerin absorption and transport, and a silicon polymer matrix affixed thereto, the silicone polymer matrix being of cross-linked silicone rubber having from about 10 to 200 micron microsealed compartments being formed by in situ cross-linking of the silicone rubber after it is mixed with the hydrophilic solvent system containing the nitroglycerin and the hydrophobic solvent system which enhances nitroglycerin transport and dispersion, the nitroglycerin being diffusible through the biologically acceptable silicon polymer matrix at a therapeutically effective constant rate when the microsealed nitroglycerin pad is affixed to the skin, said hydrophilic solvent being non-diffusible through the biologically acceptable polymer matrix.

A most preferred embodiment of the present invention is a microsealed, transdermal nitroglycerin delivery device comprising a biologically acceptable silicone polymer matrix constructed of silicone polymers represented by the formula:

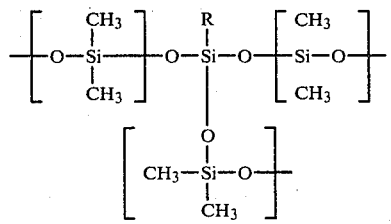

wherein R is alkoxy, alkyl, phenyl, vinyl or allyl and wherein n is about 100 to 5000 and wherein the biologically acceptable silicone polymer matrix has microsealed compartments distributed throughout, said microsealed compartments containing from 6 to 22 weight percent of 10 weight percent nitroglycerin mixed with lactose in a hydrophilic solvent system comprising water, from 10 to 30 volume % polyethylene glycol, and from 5 to 15 weight percent of a hydrophobic solvent selected from the group consisting of mineral oil, oils derived from coconut oil or mixtures thereof. Representative coconut oil derivatives include isopropyl palmitate and miglyol oil. The microsealed compartments are formed by in situ cross-linking of the liquid silicone polymer after it is emulsified with the hydrophilic solvent system containing the nitroglycerin and the hydrophobic solvent.

Generally speaking, to prepare the transdermal nitroglycerin pad of the present invention, a saturated solution of a 10 percent nitroglycerin-lactose mixture is prepared in a suitable hydrophilic solvent system such as 10–30 (v/v) percent polyethylene glycol 400 in distilled water. An excess amount of the nitroglycerin-lactose mixture is maintained in this preparation to obtain a uniform paste after manual or mechanical mixing for approximately 5–10 minutes. This uniform paste is added to the silicone elastomer, i.e., MDX 4-4210 elastomer, Dow Corning, Midland, Mich. along with the required amount of a hydrophobic solvent or a similar solvent mixture, such as mineral oil, isopropyl palmitate, or a mixture thereof. All of these ingredients are mixed from 5 to 15 minutes in a low shear, explosion-proof mixing vessel maintained under a vacuum of from 45–70 cm. The polymerizing catalyst is added and mixing is continued under vacuum from about 15 to 30 minutes. The final mixture is viscous, and is poured, with the aid of mixing equipment, into clean, dry stainless steel plates. In the case of 2×4 cm pads, suitable amounts of the final mixture are poured into 12″ by 12″ stainless steel plates fitted with a frame of a desired thickness ranging from 5.0 mm to 1.2 mm. A suitable material, such as aluminum foil, is placed on the poured material and top plates having the same dimensions as the bottom plates, but without frames, are pressed to fill the molds with the polymerizing formulation. The molds are secured in place with screws in four corners and placed in an air circulating oven at about 60° C. After two hours, the molds are removed, cooled, and the cured pad material adhering to the aluminum foil is pulled off, cut into suitable size pads, e.g. 2×4 cm with aluminum foil backing. The pads are then stored in air tight containers.

The pads preferably contain from about 6 to about 22 weight percent of a commercially available 10 percent niroglycerin-lactose mixture to provide the optimum, transdermal dosage. The optimum dosage was determined both from a series of bioavailability studies with neat nitroglycerin as well as with pads of the present invention of differing dosages and thicknesses, as described in detail in the examples hereinbelow.

The following examples further illustrate the present invention.

EXAMPLE 1

A 10 percent nitroglycerin-lactose mixture (55 g), labeled with $C^{14}$ nitroglycerin, was mixed for about 5 minutes with 25.0 g of 10 percent (v/v) polyethylene glycol 400 solution in deionized water. A uniform paste of the above mixture was added to 157.5 g of MDX 4-4210 silicone elastomer (Dow Corning, Midland, Mich.). Upon intial mixing for about 10 minutes under deaeration, a uniform dispersion was obtained in a low shear mixer. To this dispersion was added 12.5 g of the curing agent for the MDX 4-4210 elastomer and mixing was continued for another 15 minutes. The final mixture was poured into 12"×12" stainless steel plates with a 5 cm frame to hold the curing material. Aluminum foil (12"×12") was placed into each plate and pressed into the mold with a 12"×12" stainless steel plate. The molds were secured with screws affixed on four corners and placed in an air-circulating oven at about 60° C. for approximately two hours. Upon cooling, the polymer matrix, adhering to the aluminum foil as a backing, was removed from the molds and cut into 1.6×3.2 cm pads which were stored in air tight containers until use.

EXAMPLE 2

A 10 percent nitroglycerin-lactose mixture (22 g), labeled with $C^{14}$-nitroglycerin, was mixed for about 5 minutes with 8 g of a 10 percent (v/v) polyethylene glycol solution in deionized water. A uniform paste of these ingredients and 20 g of mineral oil were added to 45 g of MDX 4-4210 silicone elastomer. Upon initial mixing for 10 minutes under deaeration, a uniform dispersion was obtained in a low shear mixer. To this mixture, 5 g of the curing agent were added and the mixing was continued for about fifteen minutes under deaeration. The final mixture was poured into stainless steel plates fitted with a 5 mm thick frame. A 12"×12" piece of aluminum foil was placed on top and the mold top plates were placed thereon, pressed and secured with screws affixed on four corners. The molds were placed in an air circulating oven at 60° C. for approximately two hours. Upon cooling, the polymer matrix adhering to the aluminum backing was removed from the mold, cut into 1.6×3.2 cm pads and stored in air tight containers until use.

EXAMPLE 3

Nitroglycerin pads (1.6×1.6 cm) were prepared following the method of Example 2 from 11 g of 10 percent nitroglycerin-lactose, labeled with $C^{14}$-nitroglycerin, 4.0 g of 10 percent (v/v) polyethylene glycol 400 in deionized water, 27.5 g of MDX 4-4210 silicone elastomer, 5.0 g of isopropyl palmitate and 2.5 of curing agent. The pads were stored in airtight containers.

EXAMPLE 4

Following the method of Example 2, 2×4 cm nitroglycerin pads were prepared from 22 g of 10 percent $C^{14}$-labeled nitroglycerin-lactose, 8.0 g of 10 percent (v/v) polyethylene glycol 400-deionized water solution, 20.0 g of miglyol 812 oil, 45.0 g of MDX 4-4210 silicone elastomer and 5.0 g of curing agent. The pads were stored in airtight containers until use.

EXAMPLE 5

Nitroglycerin pads (2×4 cm) were prepared following the method of Example 2 from 11 g of $C^{14}$-labeled nitroglycerin-lactose mixture, 7 g of 10 percent (v/v) polyethylene glycol 400 in deionized water. A uniform paste of the above ingredients and a mixture of 13.0 g of isopropyl palmitate and 6.0 g of mineral oil were added to 57 g of MDX 4-4210 silicone elastomer and, fillowing initial mixing, 6.0 g of the curing agent was added and the procedure of Example 2 followed thereafter. The pads were stored in airtight containers until use.

EXAMPLE 6

Nitroglycerin pads (2×4 cm) were prepared following the method of Example 2 from 11 g of $C^{14}$-labeled 10 percent nitroglycerin-lactose, 4 g of 10 percent (v/v) polyethylene glycol 400 in deionized water, 5.0 g of isopropyl palmitate, 5.0 g of mineral oil, 22.5 g of MDX 4-4210 silicone elastomer and 2.5 g of curing agent. The pads were stored in airtight containers until use.

EXAMPLE 7

Following the method of Example 2, 2×4 and 1.6×1.6 cm nitroglycerin pads were prepared from 5.5 g of a $C^{14}$-labeled 10 percent nitroglycerin-lactose mixture, 4.0 g of polyethylene glycol 400 in deionized water, 7.5 g of isopropyl palmitate, 5.0 g of mineral oil, 25.5 g of MDX 4-4210 silicone elastomer and 2.5 g of curing agent. The pads were stored in airtight containers until use.

EXAMPLE 8

Following the method of Example 2, 2×4 cm pads were made from 3 g of $C^{14}$-labeled nitroglycerin in a 10 percent nitroglycerin-lactose mixture, 2.25 g of 10 percent (v/v) polyethylene glycol 400 in deionized water, 5.0 g of isopropyl palmitate, 5.0 g of mineral oil, 31.5 grams of MDX 4-4210 silicone elastomer (Dow Corning, Midland, Mich.) and 3.25 g of the curing agent. The pads were stored in airtight containers until use.

EXAMPLE 9

Following the method of Example 2, 2×4 cm nitroglycerin pads were prepared from 3 g of $C^{14}$-labeled nitroglycerin in a 10 percent nitroglycerin-lactose mixture, 2.5 g of 10 percent (v/v) polyethylene glycol 400 in deionized water, 7.5 g of isopropyl palmitate, 5.0 g of mineral oil, 29.5 g of MDX 4-4210 silicone elastomer and 2.75 g of curing agent. The pads were stored in airtight containers until use.

EXAMPLE 10

Studies to determine the topical availability of nitroglycerin were carried out in vivo with the rhesus monkey (*Macaca mulata*). Percutaneous absorption in this animal model has been shown to be similar to man for a number of compounds.

The animals were placed in metabolism chairs for the length of time of the dose application. Urine was collected while the animals were still in the metabolism chairs. After the dose was removed, the animals were moved to a metabolism cage for continued urine collection.

Nitroglycerin, labeled with carbon-14, was applied to the skin. The site of application can be any part of the body; however, the ventral forearm or upper part of the inner arm was used for convenience. The area of application is generally small, i.e., 2–10 $cm^2$; however, any area can be used. The final concentration is expressed as an amount per unit area of skin (i.e. 1.0 mg/1 $cm^2$).

In the case of liquid, cream or ointment formulations, the dose was spread over the exact skin area. In the case of the pads of the present invention, they were taped to the skin. In the case of liquids, cream or ointments, the treated area was covered with aluminum foil and tape. In all cases, the tape and foil and where applicable the nitroglycerin pads were removed after 24 hours and the site of application was wiped three times with gauze soaked with ethanol, then washed with soap and water.

Absorption is quantified on the basis of the percent of radioactivity excreted in urine for 3 days following application of a known amount of the labeled nitroglycerin to the skin. Daily urinary excretion values are collected for excretion of radioactivity by other routes and retention of radioactivity in the body by the administration of an intravenous dose of $C^{14}$-labeled nitroglycerin according to the following formula:

prepared according to the methods of Examples 1–9 are set forth in Table II. In Table II, the transdermal nitroglycerin pads are referred to as MDD-N.G. N.G. stands for nitroglycerin.

TABLE II

MDD-($C^{14}$) Nitroglycerin Lot Composition And Their In-Vivo Bioavailability In The Monkey
weight/weight %
MDD-N.G. ($C^{14}$) Lot Composition

| Ingredients | | | | | | | | | | | | |
|---|---|---|---|---|---|---|---|---|---|---|---|---|
| 10% N.G. ($C^{14}$)/lactose | 22 | 22 | 22 | 22 | 22 | 11 | 11 | 11 | 11 | 11 | 6 | 6 |
| 10% PEG 400/H$_2$O | 10 | 8 | 8 | 8 | 8 | 8 | 8 | 8 | 8 | 7 | 4.5 | 4.5 |
| IPP | — | — | — | 10 | 10 | 15 | 10 | 15 | 8 | 13 | 15 | 10 |
| Mineral Oil | — | — | 20 | 10 | — | — | 10 | 10 | 8 | 6 | 10 | 10 |
| MDX 4-4210 | 63 | 45 | 45 | 45 | 55 | 60 | 56 | 51 | 59 | 57 | 59 | 63 |
| Curing Agent | 5 | 5 | 5 | 5 | 5 | 6 | 5 | 5 | 6 | 6 | 5.5 | 6.5 |
| Niglyol 812 | — | 20 | — | — | — | — | — | — | — | — | — | — |
| In Vivo Parameter Data | | | | | | | | | | | | |
| $C^{14}$ Recovered in Urine % | 4.9 | 4.6 | 9.4 | 27.7 | 28.1 | 37.4 | 51.2 | 34.0 | 40.6 | 32.2 | 47.9 | 35.0 |
| $C^{14}$ Released from MDD % | — | 12.9 | 15.6 | 31.7 | 27.4 | 40.6 | 52.5 | 36.5 | 47.4 | 40.3 | 55.8 | 37.5 |
| Dose (mg) (+ 0–20% Excess) | 64 | 64 | 64 | 64 | 64 | 16 | 16 | 16 | 16 | 16 | 6.4 | 6.4 |
| Thickness (cm) | 0.6 | 0.6 | 0.6 | 0.6 | 0.6 | 0.25 | 0.25 | 0.25 | 0.25 | 0.2 | 0.25 | 0.25 |
| Size (cm) | 1.6 × 3.2 | 1.6 × 3.2 | 1.6 × 3.2 | 1.6 × 3.2 | 1.6 × 3.2 | 2 × 4 | 2 × 4 | 2 × 4 | 2 × 4 | 2 × 4 | 2 × 4 | 2 × 4 |

Percent Absorption =

$$\frac{\% \text{ dose of radioactivity in urine from topical}}{\% \text{ dose of radioactivity in urine from IV}} \times 100$$

In the case of $C^{14}$-labeled nitroglycerin applied via the nitroglycerin pad of the present invention, the device can be removed from the skin and analyzed for residual radioactivity. The amount of radioactivity which has been removed from the device, by comparative assays with devices not appld to skin, is considered to have been released in vivo during the time of skin application. Analysis for radioactivity can be conducted using any commercially available liquid scintillation counter. To determine the amount of radioactivity in this study, 1.0 ml of radioactive urine was mixed with scintillation fluid (10 ml of PCS solubilizer, Amersham Corporation, Arlington Heights, Ill.). The urine mixed with scintillant is counted for radioactivity in a liquid scintillation counter and the amount of radioactivity determined.

The results of neat nitroglycerin absorption are set forth in Table I. The data show that if the topical concentration of nitroglycerin increases from 0.1 to 1.0 mg/cm$^2$ skin area, the bioavailability of nitroglycerin remains equal to or greater than 40% for a 24 hour applicaton. Topical concentrations of 7 and 10 mg/cm$^2$ showed decreased absorption and it was concluded that the maximum optimum dosage for good bioavailability is 5 mg/cm$^2$.

TABLE I

Percutaneous Absorption of $C^{14}$ Nitroglycerin: Topical Concentration Versus Absorption for Neat Liquid Application

| Topical Concentration mg/cm$^2$ | Percent Dose Absorbed Mean + SEM |
|---|---|
| 0.01 | 41.8 ± 3.2 |
| 0.1 | 43.5 ± 3.3 |
| 1.0 | 36.6 ± 3.7 |
| 7.0 | 22.6 ± 4.2 |
| 10.0 | 7.8 ± 0.7 |

The data for the in vivo release and bioavailability of nitroglycerin from the transdermal nitroglycerin pads Literature reports on topical nitroglycerin ointment suggest an effective clinical response from approximately 20 to 40 mg of nitroglycerin (*Cardiology:* 63 337,1978; *American Heart J.* 96: 578,1978).

It will be apparent to those skilled in the art that the nitroglycerin pads of Examples 1–9 were prepared with $C^{14}$-labeled nitroglycerin for purposes of bioavailability studies and that the pads are normally prepared with unlabeled nitroglycerin. It will also be apparent to those skilled in the art that the lactose mixture is used for ease and safety of handling.

EXAMPLE 11

275 Grams of 10% nitroglycerin-lactose mixture was mixed with 175.0 g of 10% (v/v) polyethylene glycol 400 in deionized water. A uniform paste of these ingredients, 325.0 g of isopropyl palmitate, 150.0 g of mineral oil and 150 g of curing agent for MDX 4-4210 were added to 1425.0 g of silicone elastomer MDX 4-4210. The mixture was mixed for 5 minutes without deaeration in a helicone 4 CV mixer (Atlantic Research Corporation, Gainesville, VA) and the mixing was continued under a vacuum of about 60–70 cm for 30 minutes. The final mix was poured in suitable amounts (100–140 g) into 12"×12" stainless steel plates with 1.3 mm frames. Aluminum foil was placed atop the poured material in each plate and pressed into the molds with 12"×12" plates. The molds were secured with screws affixed on four corners and then placed in an air circulating oven at 60° C. for about two hours. Upon cooling, the cured polymer matrix adhering to the aluminum foil was removed from the molds, stored overnight covered with aluminum foil, and cut into 2×4" pads of approximately 2 mm thickness. The pads were packaged in SURLYN ® laminated foil (Ludlow Co., Lombard, Ill.) and stored in suitable containers.

We claim:

1. A microsealed, nitroglycerin pad suitable for transdermal administration of nitroglycerin comprising a backing, a biologically acceptable silicone polymer matrix affixed to said backing, said silicone polymer matrix being of cross-linked silicone rubber having a plurality of 10 to 200 micron microsealed compartments therein, and containing therein from 10 to 30 volume percent of an aqueous hydrophilic solvent system comprising from about 6 to 22 weight percent of a mixture containing 10 weight percent nitroglycerin mixed with lactose therein, and from 5 to 15 weight percent of a hydrophobic solvent system, said hydrophobic solvent system being selected from the group consisting of mineral oil, a triglyceride of a saturated coconut oil acid and mixtures thereof, and said hydrophilic solvent being a polyethylene glycol.

2. The nitroglycerin pad of claim 1 wherein said hydrophilic solvent system is an aqueous polyethylene glycol 400 solution.

3. The nitroglycerin pad of claim 2 wherein said hydrophobic solvent is isopropyl palmitate.

4. The nitroglycerin pad of claim 2 wherein said hydrophobic solvent is mineral oil.

5. The nitroglycerin pad of claim 2 wherein said hydrophobic solvent compriese isopropyl palmitate and mineral oil.

6. The nitroglycerin pad of claim 2 wherein said hydrophobic solvent is mineral oil and migloyl oil.

* * * * *